(12) United States Patent
Haywood et al.

(10) Patent No.: US 11,471,616 B2
(45) Date of Patent: Oct. 18, 2022

(54) DEVICE AND METHOD TO LOCATE SITE OF INTRAMUSCULAR INJECTION

(71) Applicant: Becton, Dickinson and Company, Franklin Lakes, NJ (US)

(72) Inventors: Regina Haywood, Franklin Lakes, NJ (US); Brad E. Noe, Randolph, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 340 days.

(21) Appl. No.: 16/801,800

(22) Filed: Feb. 26, 2020

(65) Prior Publication Data

US 2020/0276396 A1 Sep. 3, 2020

Related U.S. Application Data

(60) Provisional application No. 62/812,942, filed on Mar. 1, 2019.

(51) Int. Cl.
*A61M 5/42* (2006.01)
*A61M 5/00* (2006.01)
(Continued)

(52) U.S. Cl.
CPC ......... *A61M 5/427* (2013.01); *A61B 17/3403* (2013.01); *A61M 5/002* (2013.01); *A61M 5/46* (2013.01); *A61B 2017/3411* (2013.01); *A61M 2205/02* (2013.01); *A61M 2205/33* (2013.01); *A61M 2205/58* (2013.01); *A61M 2210/083* (2013.01)

(58) Field of Classification Search
CPC ...... A61M 5/427; A61M 5/002; A61M 5/178; A61M 5/46; A61M 2205/02; A61M 2205/33; A61M 2205/58; A61M 2210/083; A61B 2017/3411; A61B 17/3403; A61B 2034/108
See application file for complete search history.

(56) References Cited

U.S. PATENT DOCUMENTS

D261,302 S 10/1981 Wheeler
D322,125 S 12/1991 Dorsey
(Continued)

FOREIGN PATENT DOCUMENTS

CN 104667389 A * 6/2015
CN 104667389 A 6/2015
(Continued)

OTHER PUBLICATIONS

Cook, Ian F., "An evidence based protocol for the prevention of upper arm injury related to vaccine administration (UAIRVA)", Human Vaccines (2011), 7:8, pp. 845-848.
(Continued)

*Primary Examiner* — Nathan R Price
*Assistant Examiner* — Anh Bui
(74) *Attorney, Agent, or Firm* — Servilla Whitney LLC (57) ABSTRACT

Devices, kits and methods for determining the site of intramuscular injection in adult and child patients are disclosed. The device includes a top element and two legs that are configured to be fastened in a first position and a second position. When placed in the first position and second position, the device forms a substantially triangular region having a center that corresponds to the site of injection.

14 Claims, 5 Drawing Sheets

(51) Int. Cl.
*A61M 5/46* (2006.01)
*A61B 17/34* (2006.01)

(56) References Cited

U.S. PATENT DOCUMENTS

| | | |
|---|---|---|
| D379,657 S | 6/1997 | Pretel et al. |
| 5,732,474 A * | 3/1998 | Cannon .................. G01B 3/563 |
| | | 33/456 |
| 6,238,411 B1 * | 5/2001 | Thorner ................ A61M 29/00 |
| | | 606/199 |
| 6,643,942 B1 * | 11/2003 | Russell ................... G01C 9/28 |
| | | 33/459 |
| D647,206 S | 10/2011 | Massad |
| 8,047,201 B2 | 11/2011 | Guyuron et al. |
| D664,655 S | 7/2012 | Daniel et al. |
| D682,425 S | 5/2013 | Nunes et al. |
| D723,397 S | 3/2015 | Quint, Jr. |
| D750,776 S | 3/2016 | Lytle et al. |
| 9,398,919 B2 | 7/2016 | Aram et al. |
| D782,351 S | 3/2017 | Zahora |
| D806,587 S | 1/2018 | Fishburne, Jr. |
| 11,092,439 B2 * | 8/2021 | Woryk ..................... G01B 3/06 |
| D933,506 S | 10/2021 | Kurani et al. |
| 2014/0039451 A1 | 2/2014 | Bangera et al. |
| 2018/0133403 A1 * | 5/2018 | Schneider ........... A61M 5/3257 |
| 2020/0149856 A1 * | 5/2020 | Miller ...................... G01C 9/34 |
| 2020/0276396 A1 | 9/2020 | Haywood et al. |

FOREIGN PATENT DOCUMENTS

| | | | |
|---|---|---|---|
| GB | 2234715 A * | 2/1991 | ............ B43L 11/045 |
| GB | 2234715 A | 2/1991 | |

OTHER PUBLICATIONS

PCT International Search Report and Written Opinion in PCT/US2020/020038 dated May 26, 2020, 13 pages.

* cited by examiner

DEVICE AND METHOD TO LOCATE SITE OF INTRAMUSCULAR INJECTION

CROSS-REFERENCE TO RELATED APPLICATIONS

This application claims priority to U.S. Provisional Application No. 62/812,942, filed Mar. 1, 2019, the entire disclosure of which is hereby incorporated by reference herein.

BACKGROUND

The continuation of unsafe injection practices in healthcare applications puts patients and healthcare providers in hospitals, clinics, practices and elsewhere at risk for largely preventable negative health effects. For example, a common procedure is a deltoid intramuscular injection, which can be conducted in various locations such as in pharmacies, clinics, physicians' offices and hospitals. Other sites for intramuscular injections include the vastus lateralis (thigh) muscle, ventrogluteal site (hip), and the dorsogluteal site (buttock). Muscles have larger and more blood vessels than subcutaneous tissue and injections here usually have faster rates of absorption than subcutaneous injections or intradermal injections.

The individual performing the intramuscular injection, who is typically a health care practitioner such as a doctor, a nurse, a medical technician, a pharmacist, or other provider such as a family member, acquaintance or roommate of the patient, must be aware of the proper location for the injection and the neurovascular structures present within the region of the injection. For deltoid injections, the deltoid mass is relatively small compared to other intramuscular injection sites, and therefore, resulting in a small margin for error at the deltoid site.

The deltoid muscle is a generally accepted site for the injection of vaccines in children aged 12-18 months, older children and adults. It is extremely important to accurately identify the safe zone for injection. Upper arm injury can be a complication of an improper deltoid muscle injection. Problems with injection in the incorrect site of a deltoid injection include injection site reactions such as pain, erythema, induration and swelling at the injection site. Problems arise due to injection of the anatomical structures within or near the deltoid muscle, including the subdeltoid/subacromial bursa, anterior branch of the axillary nerve and the radial nerve. These issues are due to lack of awareness of these structures within and near the deltoid muscle.

Figure 1:
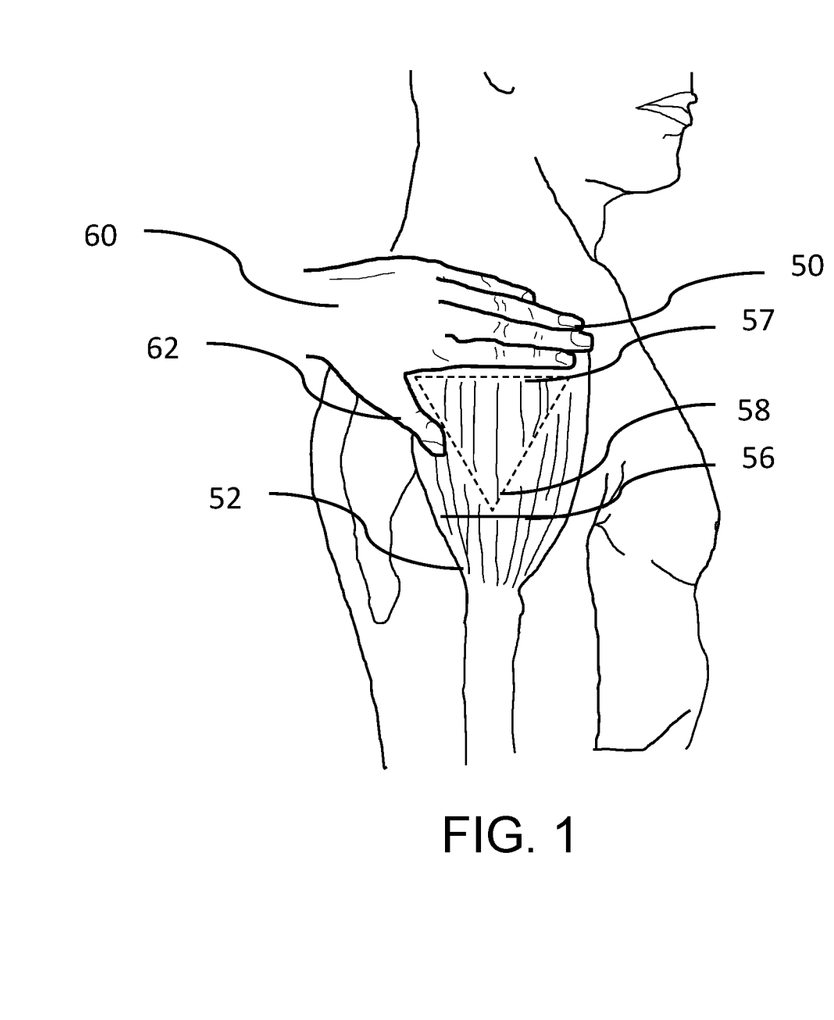
FIG. 1 illustrates the deltoid region of a patient.

Various methods exist to locate the safe zone for a deltoid injection, which can be found in medical and nursing textbooks, on the internet and in journals, but they all involve unacceptable variability and uncertainty. There is no universally accepted agreement on the particular location of the injection, and a variety of distances below the acromion have been recommended. FIG.1 shows anatomical markers that may be used to determine the injection site for a deltoid injection. At least one author indicates that injection into the site midway between the acromion 50 and the deltoid tuberosity 52 is preferred to achieve injection in the deltoid muscle 54. McGarvey MA, Hooper AL. The deltoid intramuscular injection site in the adult—current practice among general practitioners and practice nurses. Ir Med J. 2005; 98:105-7. One method is for the practitioner giving the injection to draw an imaginary a safe zone square, which represents the safe zone of injection. The top of the square is about one or two finger widths below the acromion 50, and the bottom of the deltoid square is at the insertion of the deltoid muscle approximately from the fold of the axilla 56. The optimal site of injection is at the middle portion of this square. Another way for an individual to determine the site of injection is to locate the acromion 50 and to draw a line laterally across the deltoid muscle from the apex of the axilla. Some medical literature has recommended visualizing the base 57 of a triangle 58 on the acromion 50. However, other medical literature has recommended placing the base 57 of the triangle two to three finger breadths below the acromion 50 as shown in FIG. 1. A practitioner can use their hand 60 as shown in FIG. 1 with the thumb 62 extended to form a partial outline of the imaginary triangle 58. The injection site is the midpoint of the triangle.

The variety of techniques to locate a safe deltoid injection site leads to uncertainty and guesswork in making deltoid injections. For example, there is uncertainty with respect to where the practitioner is place their fingers. Many practitioners who administer immunization injections do not frequently administer deltoid injections and lack proficiency to determine the proper site of injection. In addition, variation in the size of hands and fingers of various practitioners can lead to further uncertainty in making proper deltoid injections. There is a need to provide a device and a method that provides greater certainty and repeatability in determining the site of deltoid injections to reduce the frequency of problems such as injection of the subdeltoid/subacromial bursa, anterior branch of the axillary nerve and the radial nerve.

SUMMARY OF THE DISCLOSURE

One aspect of the present disclosure provides a device to locate an intramuscular site of an injection comprising a top element including a first end and a second end, and a top edge configured to be placed adjacent to a patient's acromion; a second leg pivotally attached to the first end of the top element such that the first leg has an attached end and a free end; a second leg pivotally attached to the second end such that the first leg has an attached end and a free end; an end fastener pair including a first portion attached adjacent to the free end of the first leg and a second portion attached adjacent to the free end of the second leg, and an intermediate fastener pair including a first portion attached on the first leg between the first portion of the end fastener and the attached end of the first leg, the intermediate fastener pair including a second portion attached on the second leg between the second portion of the end fastener pair and the attached end of the second leg.

Another aspect of the disclosure pertains to an intramuscular injection kit comprising a hypodermic needle sized for intramuscular injection in a deltoid region of a patient; a syringe connectable to the hypodermic needle; and the device described herein.

One or more embodiments of the disclosure are directed to a method of locating the site of an intramuscular injection comprising: placing a top edge of a first element having a first end and a second end against the acromion of a patient; and positioning a first leg attached to the first end and a second leg attached to the second end in one of a first position and a second position to form a substantially triangular shaped region having a center, wherein when positioned in the first position, the center of the triangular region corresponds to the site of intramuscular injection for an adult patient's deltoid region, and when positioned in the second position, the center of the triangular region corresponds to the site of intramuscular injection for a child patient's deltoid region.

DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only typical embodiments of this disclosure and are therefore not to be considered limiting of its scope, for the disclosure may admit to other equally effective embodiments.

DESCRIPTION

Before describing several exemplary embodiments of the disclosure, it is to be understood that the disclosure is not limited to the details of construction or process steps set forth in the following description. The disclosure is capable of other embodiments and of being practiced or being carried out in various ways.

The term "horizontal" as used herein is defined as a plane parallel to the plane or surface of a mask blank, regardless of its orientation. The term "vertical" refers to a direction perpendicular to the horizontal as just defined. Terms, such as "above", "below", "bottom", "top", "side" (as in "sidewall"), "higher", "lower", "upper", "over", and "under", are defined with respect to the horizontal plane, as shown in the figures.

The term "on" indicates that there is direct contact between elements. The term "directly on" indicates that there is direct contact between elements with no intervening elements.

Referring now to FIGS. 2-5, a first aspect of the present disclosure pertains to a device to aid in location of an intramuscular site of an injection. In specific embodiments, the device is configured to locate the intramuscular site of injection of a patient's deltoid region.

According to one or more embodiments, the device may be used by persons of any level of skill and experience in administering intramuscular injections. The device provides a universal standard for enabling those that are not experienced or proficient in administering intramuscular injections to the deltoid region. Intramuscular injections may also be performed in a doctor's office, a hospital, a clinic or other medical facility for a variety of reasons, such as for dispensing pain medication, immunizations or other medicaments. By providing a universal standard for locating the site of injection of the deltoid region, problems associated with errant injections are reduced and/or eliminated.

In particular, the device will aid in avoiding the incorrect site of a deltoid injection, which will reduce or prevent injection site reactions such as pain, erythema, induration and swelling at the injection site. Problems, which arise due to injection of the anatomical structures within or near the deltoid muscle, including the subdeltoid/subacromial bursa, anterior branch of the axillary nerve and the radial nerve, are reduced or prevented according to one or more embodiments described herein.

According to one or more embodiments, the device includes guidance information and clearly marked reference points to align anatomically with the patient and the provider to ensure proper identification of the proper area on the patient for immunization. In some embodiments, the device can be used as a training aid, a simulator or on actual patients to ensure the correct site to successfully administer an intramuscular injection in the deltoid muscle.

The device according to one or more embodiments takes the guess work away from the individual performing the injection as to where to place their fingers to obtain the proper alignment. Many people who administer intramuscular injections do not do so with a high degree of frequency or are not as skilled with respect to proper anatomical alignment to avoid mis-administration or negative outcomes. In some embodiments, the device can be used as a job aid or clinical reference tool for intramuscular injections of the deltoid region.

In one or more embodiments, a simple and reusable device is provided that can be used in teaching, simulation or on a patient. The device according to some embodiments provides a simple yet elegant solution to textbook and two-dimensional learning. According to some embodiments, the device will improve outcomes, minimize possible negative complications and develop confidence in individuals tasked with the perilous job of administering intramuscular injections. Embodiments provide a simple to use device that includes all of the anatomically correct alignments for both adult and children patients to allow intramuscular injections in the proper site.

Figure 2:
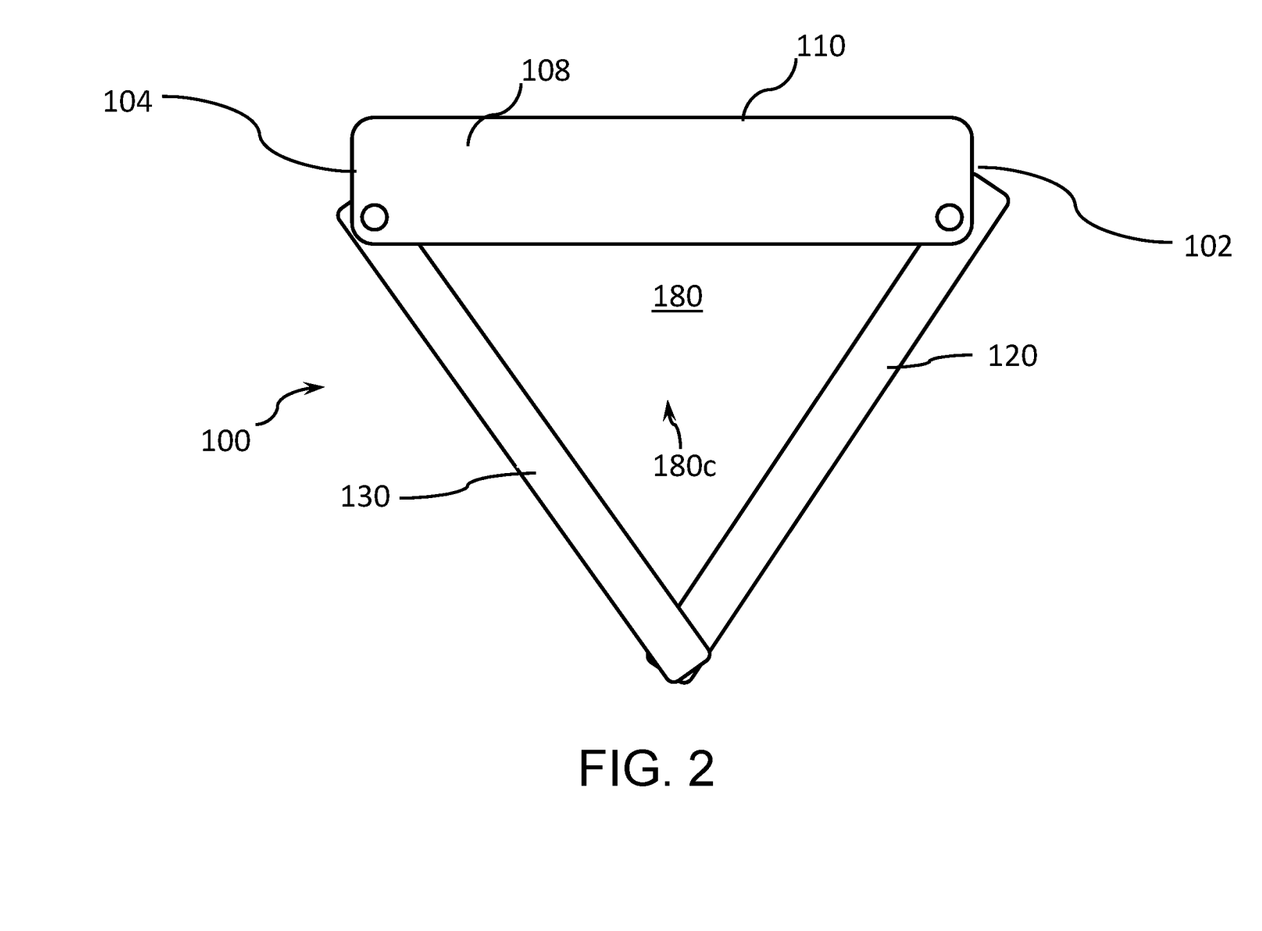
FIG. 2 illustrates a device in accordance with an embodiment of the present disclosure.
Figure 3:
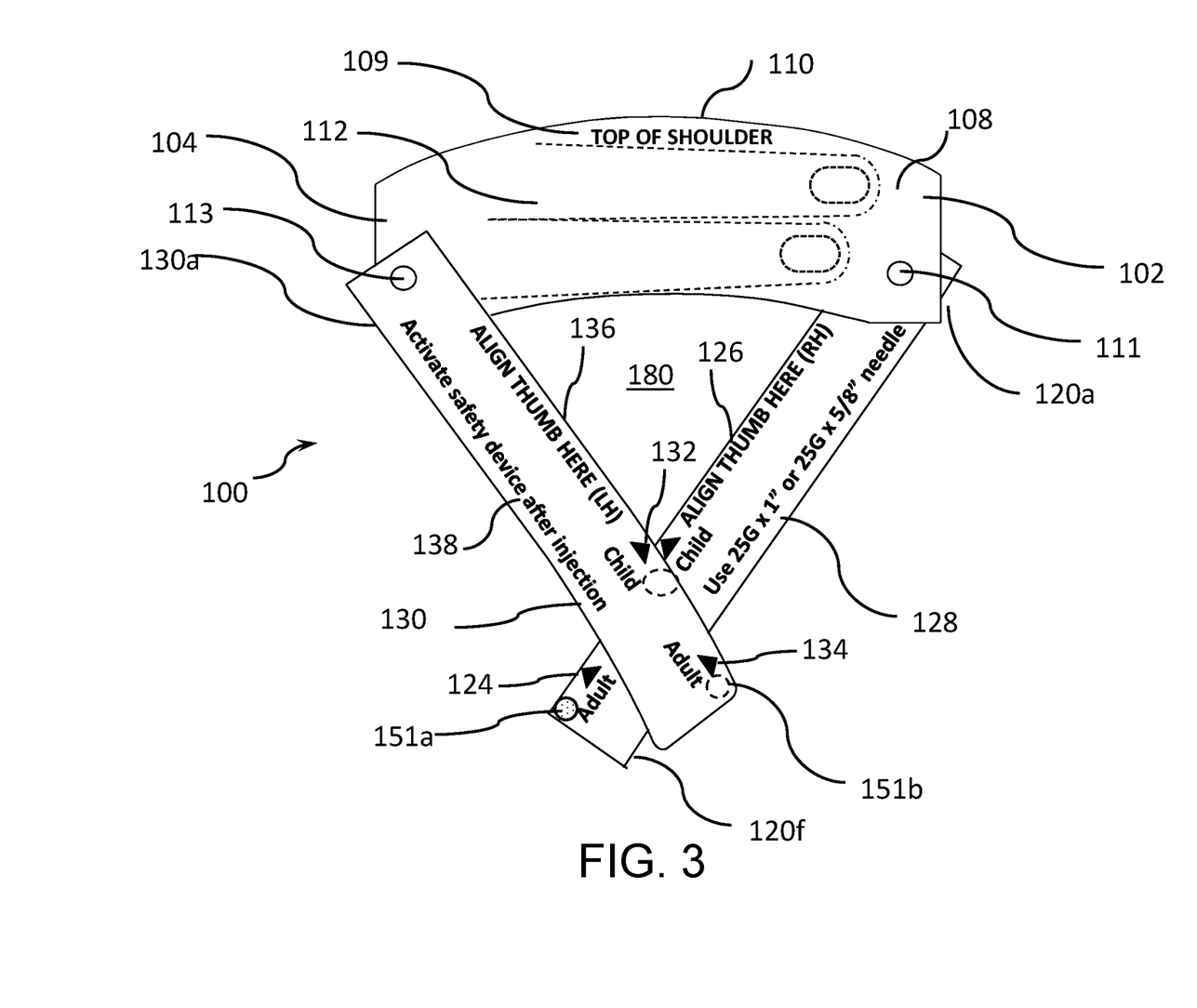
FIG. 3 illustrates a device in accordance with an embodiment of the present disclosure.
Figure 4:
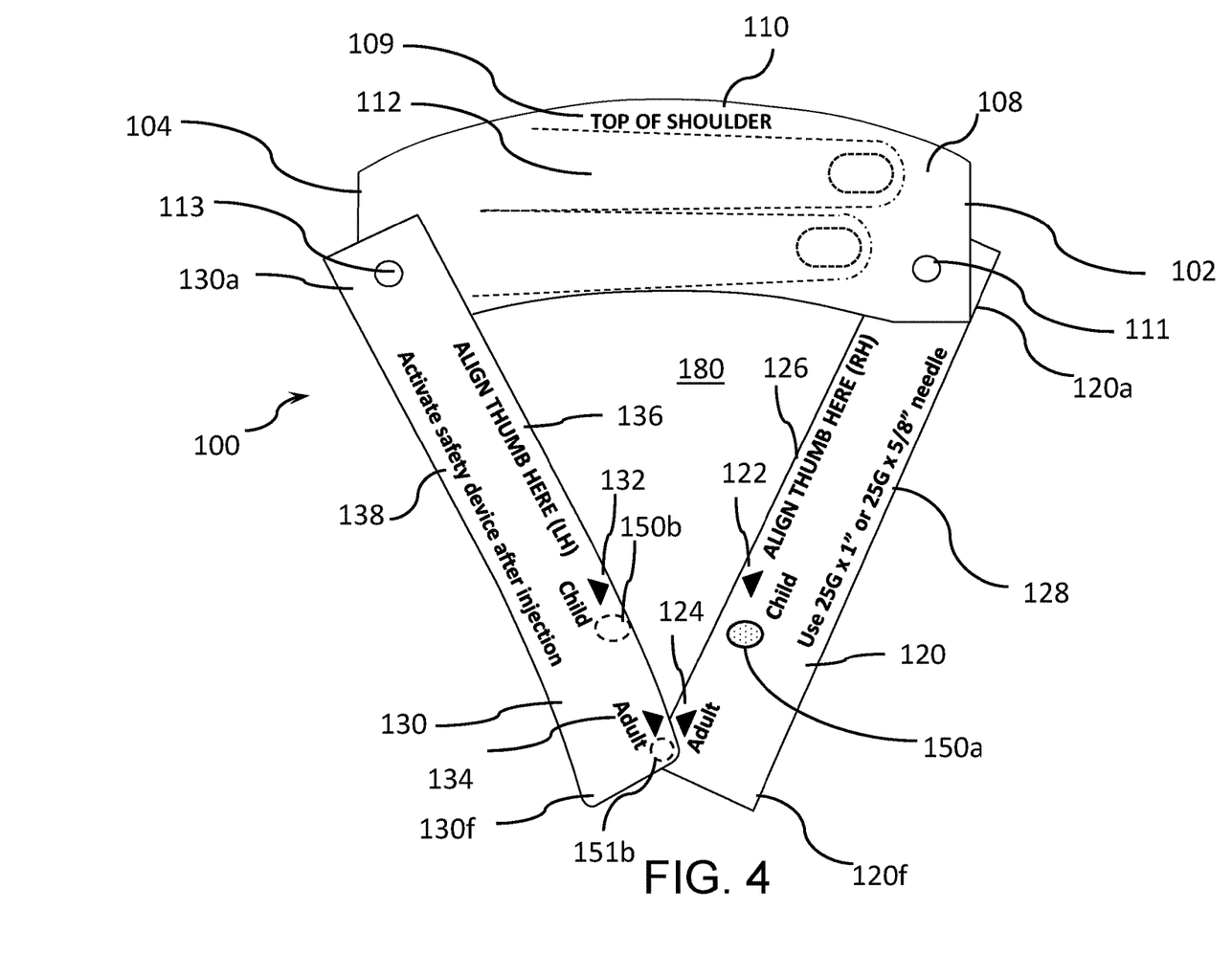
FIG. 4 illustrates a method performed in accordance with an aspect of the present disclosure.
Figure 5:
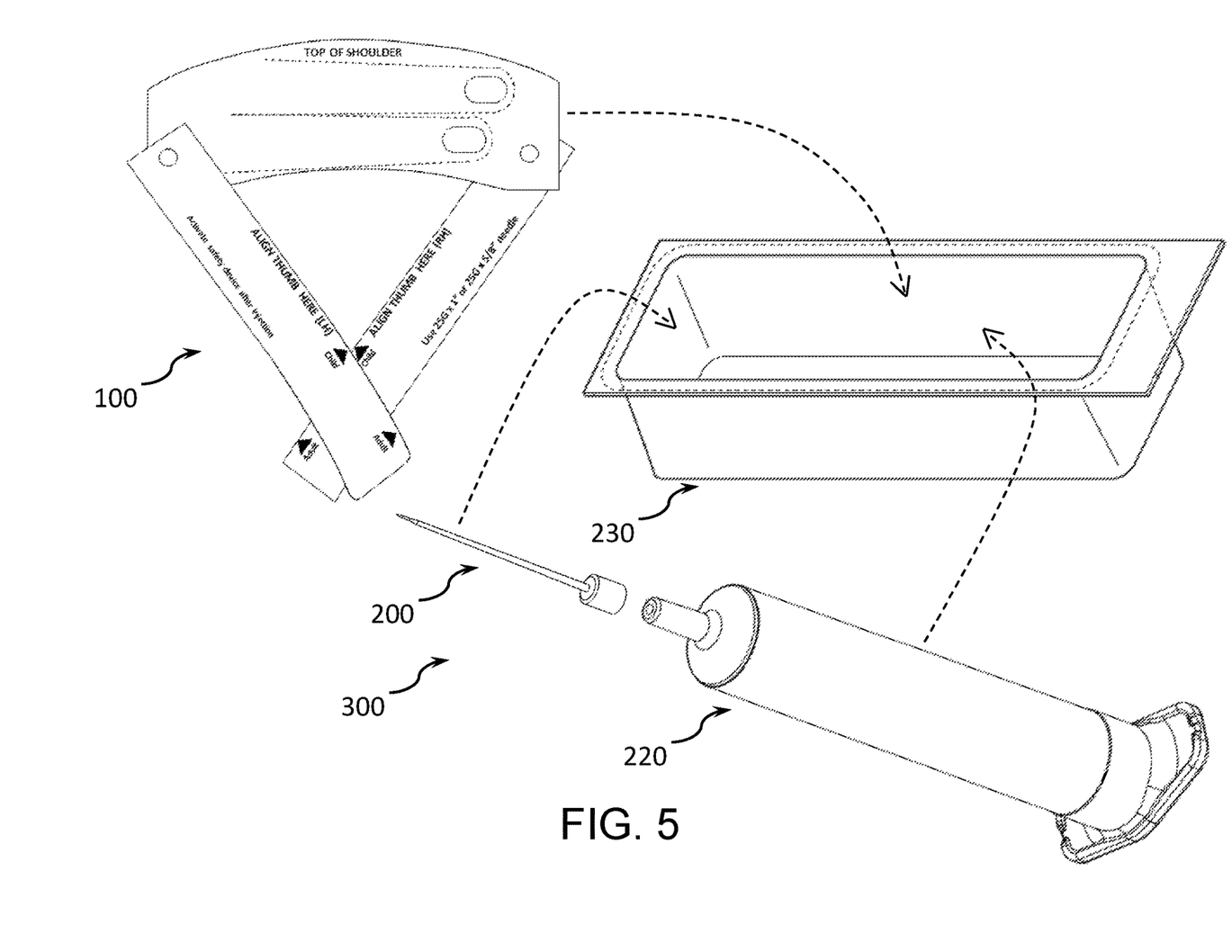
FIG. 5 illustrates a kit including a device, a hypodermic needle and a syringe in accordance with an embodiment of the disclosure.

Referring now to FIGS. 2-4, a first embodiment of the device 100 includes a top element 108 including a first end 102 and a second end 104, and a top edge 110 configured to be placed adjacent to a patient's acromion. A person of ordinary skill in the art will understand that the acromion is a bony process on the scapula, commonly known as the shoulder blade. In some embodiments, acromion placement indicia 109 is located immediately below the top edge 110 of the device 100. The acromion placement indicia 109 provides a visual marker corresponding to an anatomical reference point of a human patient so that the device is configured to locate the proper site of an intramuscular injection. The acromion indicia 109 can include words such as "TOP OF SHOULDER" as shown in FIGS. 4 and 5. Other suitable indicia can also be used to indicate where to place the device 100 for a deltoid injection.

In the embodiment shown, the device further comprises a first leg 120 pivotally attached to the first end 102 of the top element 108 such that the first leg 120 has an attached end 120a and a free end 120f. The device further comprises a second leg 130 pivotally attached to the second end 104 such that the second leg 130 has an attached end 130a and a free end 130f. The attached ends 120a and 130a can be attached to the top element 108 by any suitable attachment mechanism. For example, a rivet, a nut and bolt, or a fastening pin could be used with holes punched in the attached ends 120a and 130a and the first end 102 and the second end to aid in securing the legs 120a to the top element 108 so that the legs are pivotally attached to the top member. The legs 120 and 130 can swing freely and can be pivoted to form two different sized triangular regions, as will be described further below.

The device 100 shown in FIGS. 4 and 5 further comprise an end fastener pair including a first portion 151a attached adjacent to the free end 120f of the first leg 120 and a second portion 151b attached adjacent to the free end 130f of the second leg 130, and an intermediate fastener pair including a first portion 150a attached on the first leg 120 between the first portion 151a of the end fastener pair and the attached end 120a of the first leg 120, the intermediate fastener pair including a second portion 150b attached on the second leg 130 between the second portion 151b of the first fastener pair and the free end 130f of the second leg 130.

In one or more embodiments, the top element 108, the first leg 120 and the second leg 130 are sized such that when the end fastener pair is fastened together, the first leg 120, the second leg 130 and the top element 108 form a substantially triangular region 180 having a center 180c, wherein the center 180c (shown in FIG. 2) of the substantially triangular region 180 which corresponds to an intramuscular site of injection in the deltoid region for an adult patient when the top edge 110 of the top element 108 is place against an adult patient's acromion.

A person of ordinary skill in the art will understand that lines are drawn from each corner (or vertex) of a triangle to the midpoint of the opposite side of each vertex, then those three lines meet at a center, or centroid, of the triangle. The centroid is the triangle's center of gravity, where the triangle balances evenly. While drawing these lines is not necessary to utilize the device of the instant disclosure, this information may be useful to a user of the device to provide a visual aid in determining the proper site of intramuscular injection. There is some degree of freedom from the exact geometric center of the triangle, such that deviation from the exact geometric center will still result in a successful intramuscular injection without side effects discussed above. However, for training and explanation of the use of the device, the description of the true geometrical center of the triangle may be desired. "Substantially triangular region" refers to a region that generally corresponds to a triangle. As shown in FIGS. 3 and 4, the top element 108 has a slight degree of curvature.

In some embodiments, the top element 108, the first leg 120 and the second leg 130 are sized such that when the intermediate fastener pair is fastened together, the first leg 120, the second leg 130 and the top element 1038 form a substantially triangular region 180 having a center 180c, wherein the center 180c of the substantially triangular region corresponds to an intramuscular site of injection in the deltoid region for a child patient when the top edge of the top element is place against a child patient's acromion.

A person of ordinary skill in the art will recognize that a child patient has a smaller deltoid region than an adult patient. Therefore, the first leg 120 and the second leg 130 have a length and the end fastener pair first portion 151a and second portion 151b located adjacent to the free ends 120f, 130f of the first leg 120 and the second leg are positioned so that the triangle formed by fastening the intermediate fastener pair together generally corresponds with the deltoid region of an average adult patient. Likewise, intermediate fastener pair first portion 150a and second portion 150b are so that that the triangle 280 formed by fastening the end fastener pair together generally corresponds with the deltoid region of an average child patient.

In some embodiments, the end fastener pair comprises a hook and loop closure system, which is also known as a VELCRO® brand fastener. In some embodiments, the fastener pair may comprise a snap, which can comprise a pair of interlocking discs. Other suitable fastener pairs may include cooperating adhesive surfaces. The intermediate fastener pair according to some embodiments can comprises a hook and loop closure system, a snap, or other suitable fastener pairs such as cooperating adhesive surfaces.

Referring to FIGS. 4 and 5, in some embodiments, the top element 108 comprises finger indicia 112 to indicate a location for an individual performing the intramuscular injection to place their index finger and middle finger on the top member. In the embodiment shown, an outline of the index and middle finger of a left hand are shown as the finger indicia 112.

In some embodiments, the first leg 120 comprises right hand thumb indicia 126 to indicate a location for an individual performing the intramuscular injection to align a right thumb. The right hand thumb indicia 126 can comprise the words "ALIGN THUMB HERE (RH) or other suitable indicia.

In one or more embodiments, the second leg 130 comprises left hand thumb indicia 136 to indicate a location for an individual performing the intramuscular injection to align their left thumb. The left hand thumb indicia 136 can comprise the words "ALIGN THUMB HERE (LH) or other suitable indicia. The right hand thumb indicia 126 and left hand thumb indicia 136 may be desirable as a training aid for those individuals who have been accustomed to or trained to use the technique for locating the site of injection using their hand. Therefore, this indicia provides a useful training aid and reference points for the individual providing the injection.

In some embodiments, the first leg 120 and second leg 130 each comprises indicia 122, 132 adjacent to the end fastener pair indicating fastening the device at the end fastener pair provides an injection site location for an adult patient. As shown in FIGS. 3 and 4, the second leg 130 includes indicia 134 in the form of a triangle marker and the word "Adult" adjacent to the intermediate fastener pair second portion 150b, and the first leg 120 includes indicial 122 in the form of a triangle mark and the word "Adult" adjacent to intermediate fastener first portion 150a.

In one or more embodiments the first leg 120 and second leg 130 each comprises indicia 124, 134 adjacent to the intermediate fastener pair indicating that fastening the device at the end fastener pair provides an injection site location for a child patient. As shown in FIGS. 4 and 5, the first leg 120 includes indicia 122 adjacent to the first portion 150a of the intermediate fastener pair, and the second leg 130 includes indicia 132 adjacent to the second portion 150b of the intermediate fastener pair.

The device is configured and the indicia 132, 134 on the first leg 120 and the indicia 132, 134 on the second leg 130 are placed at a distance from the attached ends 120a, 130a of the respect first leg 120 and second leg 130 to provide anatomical reference points so that when the triangular region 180 is formed by fastening the intermediate fastener pair, the center 180c of the triangular region 180 is located at the proper site of injection for an adult patient. Likewise, when the triangular region 180 is formed by fastening the end fastener pair, the center 180c of the triangular region 180 is located at the proper site of injection for a child patient. The device provides consistent and nonvariable reference points for any individual performing an intramuscular injection at the deltoid region of an adult or child patient. The guess work has been removed, and a person providing the injection can confidently inject a patient in the deltoid region with fear of causing upper arm pain or other complications associated with injection in the improper site.

In one or more embodiments, the device 100 is made from an opaque material such as paper, cardboard or paper. Thus, the top element 108, the first leg 120 and the second leg 130 are made from an opaque material such as paper, cardboard or paper. In other embodiments, the device 100 is made from a transparent plastic or translucent plastic, which further enhances visualization when injecting the deltoid muscle. Examples of transparent plastics include, but are not limited to acrylics (e.g., polymethlamethacrylate), butyrates (e.g., cellulose acetate butyrate), polycarbonates (e.g., Lexan), and terphthalates (e.g., glycol modified polyethylene terphthalate (PETG)).

Referring now to FIG. 5, another aspect of the disclosure provides an intramuscular injection kit 300. The kit 300 comprises a hypodermic needle 200 sized for intramuscular injection in a deltoid region of a patient. In this regard, a second needle may be provided. Referring back to FIGS. 3 and 4, the device 100 can include needle indicia 128 indicating the appropriate sized needle for the injection. For example, the needle indicia 128 may state "Use 25 G×1" or 25 G by ⅝ needle" or other suitable indicia to advise the person providing the injection the proper size needle to use. The second leg 130 may include safety indicia 138 advising the individual using the device 100 to use the safety device after the injection. The safety indicia may include a message "Activate safety device after injection" or other indicia to provide for safe use of the device and the associated needle.

Referring back to FIG. 5, the kit 300 may further comprise a syringe 220 connectable to the hypodermic needle 200. The kit may further comprise a tray 230, which may comprise thermoformed plastic. The syringe 220, the hypodermic needle 220 and the device may all be placed in the tray 230, which can be sealed. The kit 300 can include any or all of the features described above with respect to the device 100.

Another aspect of the disclosure pertains to a method of locating the site of an intramuscular injection. In one or more embodiments, the method includes placing a top edge 110 of a top element 108 having a first end 102 and a second end 104 against the acromion of a patient. The method further includes positioning a first leg 120 attached to the first end 102 and a second leg attached to the second end 104 in one of a first position and a second position to form a substantially triangular region 180 having a center 180c. When positioned in the first position, the center 180c of the triangular region 180 corresponds to the proper site of intramuscular injection for an adult patient's deltoid region. It will be appreciated with respect to FIGS. 3 and 4, the first position corresponds to the end fastener pair being fastened together. When positioned in the second position, the center 180c of the triangular region 180 corresponds to the site of intramuscular injection for a child patient's deltoid region. It will be appreciated with respect to FIGS. 3 and 4 that the second position corresponds to the intermediate fastener pair being fastened together.

In some embodiments of the method, an individual administering the intramuscular injection places an index finger and a middle finger from a left hand or a right hand on finger indicia which indicates where to place the index finger and middle finger on the device, the finger indicia located on the top element 108.

In some embodiments of the method, the individual providing the injection aligns their thumb of the hand from which the index finger and middle finger has been placed on the top element on one of the first leg or the second leg. For example, if the individual administering the intramuscular injection has placed their index finger and middle finger from their right hand on the indicia of the top element, the individual aligns their thumb from their right hand with the first leg 120. Conveniently, the first leg 120 includes right hand thumb indicia 126 to aid the individual administering the injection in properly placing their thumb on the first leg 120.

Alternatively, if the individual administering the intramuscular injection has placed their index finger and middle finger from their left hand on the indicia of the top element, the individual aligns their thumb from their left hand with the second leg. Conveniently, the second leg 130 includes left hand thumb indicia 136 to aid the individual administering the injection in properly placing their thumb on the second leg 130.

In some embodiments, the method includes fastening the first leg 120 and the second leg 130 in the first position, for example, with the end fastener pair fastened together. The device is now ready to be used to provide an intramuscular injection in the deltoid region to an adult patient.

For administering an injection to a child patient, method includes fastening the first leg 120 and the second leg 130 in the second position. This can be accomplished by fastening the intermediate fastener pair. The device is now ready to use to provide a child with an intramuscular injection in the deltoid region.

The method may further comprise the individual reading indicia on the device indicating a proper size hypodermic needle for the intramuscular injection and fastening the hypodermic needle to syringe.

Reference throughout this specification to "one embodiment," "certain embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein has been described with reference to particular embodiments, it is to be understood that these embodiments are merely illustrative of the principles and applications of the present disclosure. It will be apparent to those skilled in the art that various modifications and variations can be made to the method and apparatus of the present disclosure without departing from the spirit and scope of the disclosure. Thus, it is intended that the present disclosure include modifications and variations that are within the scope of the appended claims and their equivalents.

What is claimed is:

1. A device to locate an intramuscular site of an injection comprising:
   a top element including a first end and a second end, and a top edge configured to be placed adjacent to a patient's acromion;
   a first leg pivotally attached to the first end of the top element such that the first leg has an attached end and a free end;
   a second leg pivotally attached to the second end such that the second leg has an attached end and a free end; and
   an end fastener pair including a first portion attached adjacent to the free end of the first leg and a second portion attached adjacent to the free end of the second leg, and an intermediate fastener pair including a first portion attached on the first leg between the first portion of the end fastener and the attached end of the first leg, the intermediate fastener pair including a second portion attached on the second leg between the second portion of the end fastener pair and the attached end of the second leg.

2. The device of claim 1, wherein the top element, the first leg and the second leg are sized such that when the end fastener pair is fastened together, the first leg, the second leg and the top element form a substantially triangular region having a center, wherein the center of the substantially triangular region which corresponds to an intramuscular site of injection in the deltoid region for an adult patient when the top edge of the top element is place against an adult patient's acromion.

3. The device of claim 2, wherein the top element, the first leg and the second leg are sized such that when the intermediate fastener pair is fastened together, the first leg, the second leg and the top element form a substantially triangular region having a center, wherein the center of the substantially triangular region which corresponds to an intramuscular site of injection in the deltoid region for a child patient when the top edge of the top element is place against a child patient's acromion.

4. The device of claim 2, wherein end fastener pair comprises a hook and loop closure system.

5. The device of claim 3, intermediate fastener pair comprises a hook and loop closure system.

6. The device of claim 1, wherein the top element comprises finger indicia to indicates a location for an individual performing the intramuscular injection to place their index finger and middle finger.

7. The device of claim 6, wherein the first leg comprises right hand thumb indicia to indicate a location for an individual performing the intramuscular injection to align a right thumb.

8. The device of claim 7, wherein the second leg comprises left hand thumb indicia to indicate a location for an individual performing the intramuscular injection to align their left thumb.

9. The device of claim 1, wherein the first leg and second leg each comprises indicia adjacent to the end fastener pair indicating that fastening the device at the end fastener pair provides an injection site location for an adult patient.

10. The device of claim 9, wherein the first leg and second leg each comprises indicia adjacent to the intermediate fastener pair indicating that fastening the device at the intermediate fastener pair provides an injection site location for a child patient.

11. The device of claim 1, wherein the first leg, the second leg and the top element comprise a transparent plastic.

12. The device of claim 1, wherein the first leg, the second leg and the top element comprise a translucent plastic.

13. An intramuscular injection kit comprising:
a hypodermic needle sized for intramuscular injection in a deltoid region of a patient;
a syringe connectable to the hypodermic needle; and
the device of claim 1.

14. The intramuscular injection kit of claim 13, further comprising a tray, wherein the needle, the syringe and the device are sealed in the tray.

* * * * *

UNITED STATES PATENT AND TRADEMARK OFFICE
CERTIFICATE OF CORRECTION

| | |
|---|---|
| PATENT NO. | : 11,471,616 B2 |
| APPLICATION NO. | : 16/801800 |
| DATED | : October 18, 2022 |
| INVENTOR(S) | : Regina Haywood et al. |

It is certified that error appears in the above-identified patent and that said Letters Patent is hereby corrected as shown below:

In the Specification

- Column 7, Line 20, replace "G×1" after "Use 25" and before "or" with "G X 1".

- Column 7, Line 21, replace "⅝" after "by" and before "needle" with "5/8".

Signed and Sealed this
Sixth Day of December, 2022

Katherine Kelly Vidal
*Director of the United States Patent and Trademark Office*